(12) United States Patent
Gunji

(10) Patent No.: US 8,480,977 B2
(45) Date of Patent: Jul. 9, 2013

(54) AUTOMATIC ANALYZER USING A SAMPLE CONTAINER HAVING AN INFORMATION RECORDING MEMBER

(75) Inventor: Yoshiro Gunji, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1278 days.

(21) Appl. No.: 10/844,384

(22) Filed: May 13, 2004

(65) Prior Publication Data
US 2005/0002828 A1 Jan. 6, 2005

(30) Foreign Application Priority Data

May 14, 2003 (JP) .................................. 2003-135262

(51) Int. Cl.
*B01J 3/02* (2006.01)
(52) U.S. Cl.
USPC ................ 422/509; 422/65; 422/67; 422/501
(58) Field of Classification Search
USPC .... 422/63–67, 99–104, 501, 509; 436/43–54, 436/180
See application file for complete search history.

(56) References Cited

U.S. PATENT DOCUMENTS

| | | | | |
|---|---|---|---|---|
| 5,178,834 A | * | 1/1993 | Kagayama et al. | 422/65 |
| 5,544,535 A | * | 8/1996 | Thomas | 73/864.22 |
| 6,141,602 A | * | 10/2000 | Igarashi et al. | 700/226 |
| 6,193,933 B1 | * | 2/2001 | Sasaki et al. | 422/64 |
| 6,340,588 B1 | * | 1/2002 | Nova et al. | 506/16 |
| 2002/0155616 A1 | * | 10/2002 | Hiramatsu et al. | 436/165 |

FOREIGN PATENT DOCUMENTS

| | | |
|---|---|---|
| JP | A-62-2266058 | 10/1987 |
| JP | A-02-013856 | 1/1990 |
| JP | 2-16875 | 4/1990 |
| JP | U-04-21862 | 2/1992 |
| JP | A-08-285855 | 11/1996 |
| JP | 2000-310644 | 11/2000 |
| JP | A-2002-257835 | 9/2002 |
| WO | WO 01/94016 | 12/2001 |

\* cited by examiner

*Primary Examiner* — Jill Warden
*Assistant Examiner* — Dwayne K Handy
(74) *Attorney, Agent, or Firm* — Mattingly & Malur, P.C.

(57) ABSTRACT

A sample is contained in a sample container and a physical relationship between the sample and a sample ID thereof is established. However, after the sample ID is read by a bar code reader and the sample is transferred to an analysis-dedicated small sample container, the sample ID and the sample are separated from each other. Following the end of analysis, therefore, the sample ID must be merged with a corresponding analysis result. A read/write-enable ID carrier is provided on an analysis-dedicated sample container into which the sample is pipetted or on a tank for holding the analysis-dedicated sample container. When the sample is pipetted or when the analysis-dedicated sample container is moved, the sample ID and other information are transferred to the read/write-enable ID carrier.

4 Claims, 11 Drawing Sheets

- SAMPLE RACK STOCK 1 = SAMPLE ID 1
- SAMPLE RACK STOCK 2 = SAMPLE ID 2
- SAMPLE RACK STOCK 3 = SAMPLE ID 3

AUTOMATIC ANALYZER USING A SAMPLE CONTAINER HAVING AN INFORMATION RECORDING MEMBER

BACKGROUND OF THE INVENTION

1. Field of the Invention

The present invention relates to an analysis apparatus using a sample container, which contains a sample to be analyzed and which is provided with an information recording medium for recording information regarding the sample contained in the sample container. More particularly, the present invention relates to an analysis apparatus including a mechanism for pipetting (distributively injecting) a sample contained in one sample container into a plurality of sample containers.

2. Description of the Related Art

The state of the related art will be described below in connection with, by way of example, a medical analyzer for handling living body samples, e.g., blood and urine.

In hospitals and inspection centers, a variety of inspections, such as blood inspection, biochemistry inspection and general inspection, are carried out as clinical inspections by using living body samples, e.g., blood and urine, as specimen materials. An analyzer used for those inspections generally includes a sampler (sample pipetting device) in which measurement is automatically performed after the samples are put in a sample rack and then the sample rack is set in place.

In a recent automatic analyzer, each sample container containing a sample (specimen material) therein or each sample rack for holding several sample containers together is provided with an information recording medium (ID carrier), e.g., a barcode, for recording identification information (sample ID) of the sample in the sample container so that the analyzer or an inspector can identify from whom among patients the relevant sample has been picked. The analyzer or the inspector reads the sample ID from the ID carrier, and judges the relevant sample belongs to whom among patients or what kind of analysis is required.

An actual analysis process is performed in many cases by taking (sampling) a proper amount of a parent sample required for the analysis, which is contained in the sample container, and transferring (pipetting) the picked sample into an analysis-dedicated sample container, which is suitable to perform the analysis process and is called a tube or a palette, smaller than the sample container. In this case, the (child) sample pipetted into the analysis-dedicated sample container is subjected to process steps required for making the analysis, such as mixing with a reagent and a reaction, and then analyzed to obtain an analysis result.

In the known analyzer, the ID carrier is provided only on the sample container. The reason is that most of ID carriers currently used are in the form of a read-only barcode. Because a mechanism for preparing and attaching barcodes requires a considerable installation area, it is usual to employ a device dedicated for preparing barcodes and attaching them to individual sample containers. On the other hand, the sample is pipetted into the analysis-dedicated sample container by using a sample pipetting mechanism provided in the analyzer. To prepare barcodes and attach them to individual analysis-dedicated sample containers, therefore, the mechanism for preparing and attaching barcodes must be provided for each analyzer. This is however practically difficult to realize due to an increase of the cost.

For that reason, hitherto, the ID of the child sample pipetted from the parent sample is stored in correspondence to the position in each analyzer where the sample container containing the child sample is located. Then, each analyzer merges an analyzed result with the sample ID and reports the analysis result to a host computer.

Such a construction of the known analyzer is described in, e.g., Patent Reference 1; JP,B 2-16875.

SUMMARY OF THE INVENTION

In an analyzer provided with a mechanism for pipetting a sample contained in one sample container into a plurality of sample containers (child sample containers), but not provided with means for holding sample identification information for each of the plurality of sample containers, there is a possibility that the identification information of the sample pipetted into each of the plurality of sample containers may mismatch with the sample identification information recognized by the analyzer or an operator of the analyzer. In an automatic analyzer for clinical inspections, particularly, when the analyzer operator changes the position at which the child sample container has been placed, there is a risk that the proper correspondence between the sample ID and the analysis is lost. Further, in the field of medical analysis, a demand for a capability of tracking analysis steps (i.e., traceability) is lately proposed from FDA (Food and Drug Administration) of the USA, etc. for assurance of the analysis steps. However, the currently used apparatus has a difficulty in satisfying such a demand.

Accordingly, it is an object of the present invention to provide an analysis apparatus by which, even in an analyzer provided with a mechanism for pipetting a sample contained in one sample container into a plurality of sample containers, a mismatch between the sample contained in each of the plurality of sample containers and identification information of the sample can be reliably prevented.

To achieve the above object, the present invention is constituted as follows.

Analysis apparatus of the present invention comprises a first sample container for containing a sample; an information recording medium provided on the first sample container and recording information regarding the sample contained in the first sample container; a pipetting mechanism for distributing the sample contained in the first sample container into a plurality of samples; and a second sample container for containing the sample pipetted by the pipetting mechanism, wherein the second sample container includes an information recording medium for recording information regarding the sample contained in the second sample container, and the analysis apparatus further comprises means for, when the pipetting mechanism pipettes the sample from the first sample container into the second sample container, copying at least a part of the information recorded in the information recording medium provided on the first sample container into the information recording medium provided on the second sample container.

The sample is preferably in the form of a liquid or powder so that the sample can be distributively injected by the pipetting mechanism, such as a pipette. The information recording medium can have any suitable form, but it is preferably in the form of a sheet from the viewpoint of minimizing a space occupied by the information recording medium. The meaning of the expression "includes the information recording medium (provided on)" is not limited to the case in which a sheet- or box-like information recording medium is provided directly on the sample container. Any suitable manner can be used to install the information recording medium so long as identification information regarding the content of the sample container can be read and written from the outside of the sample container. Conceivable various manners include, for example, the case of directly attaching the information recording medium to the container surface, the case of attaching it to a support for holding the sample container in its proper posture, and the case of embedding it in the support in a concealed condition when viewed from the outside. Similarly, various manners such as utilizing light and magnetism are applicable to read information.

Preferably, the analysis apparatus further comprises recording means for, when analysis of the sample has completed, recording an analysis result of the relevant sample in an information recording medium within the analysis apparatus, such as a hard disk, an electronic memory or a magnetic memory, in correspondence to the sample information recorded in the information recording medium provided on the second sample container. Alternatively, the analysis data made correspondent to the sample information may be sent to a higher-level (host) computer in the analysis apparatus for collecting and analyzing the analysis result, etc.

The pipetting mechanism may include means for reading at least a part of the information recorded in the information recording medium provided on the first sample container and writing the read information into the information recording medium provided on the second sample container, and the analysis apparatus may further comprise control means for controlling pipette operation in synchronism with read/write operation for the information recording medium. The expression "controlling pipette operation in synchronism with read/write operation" means that the pipette operation and the read/write operation are executed concurrently. To that end, the information reading/writing means may be disposed near a pipetting probe of the pipetting mechanism so that read/write of information is started at the same time when the probe is moved to come close to the sample container for pipetting the sample.

DESCRIPTION OF THE PREFERRED EMBODIMENTS

Figure 1:
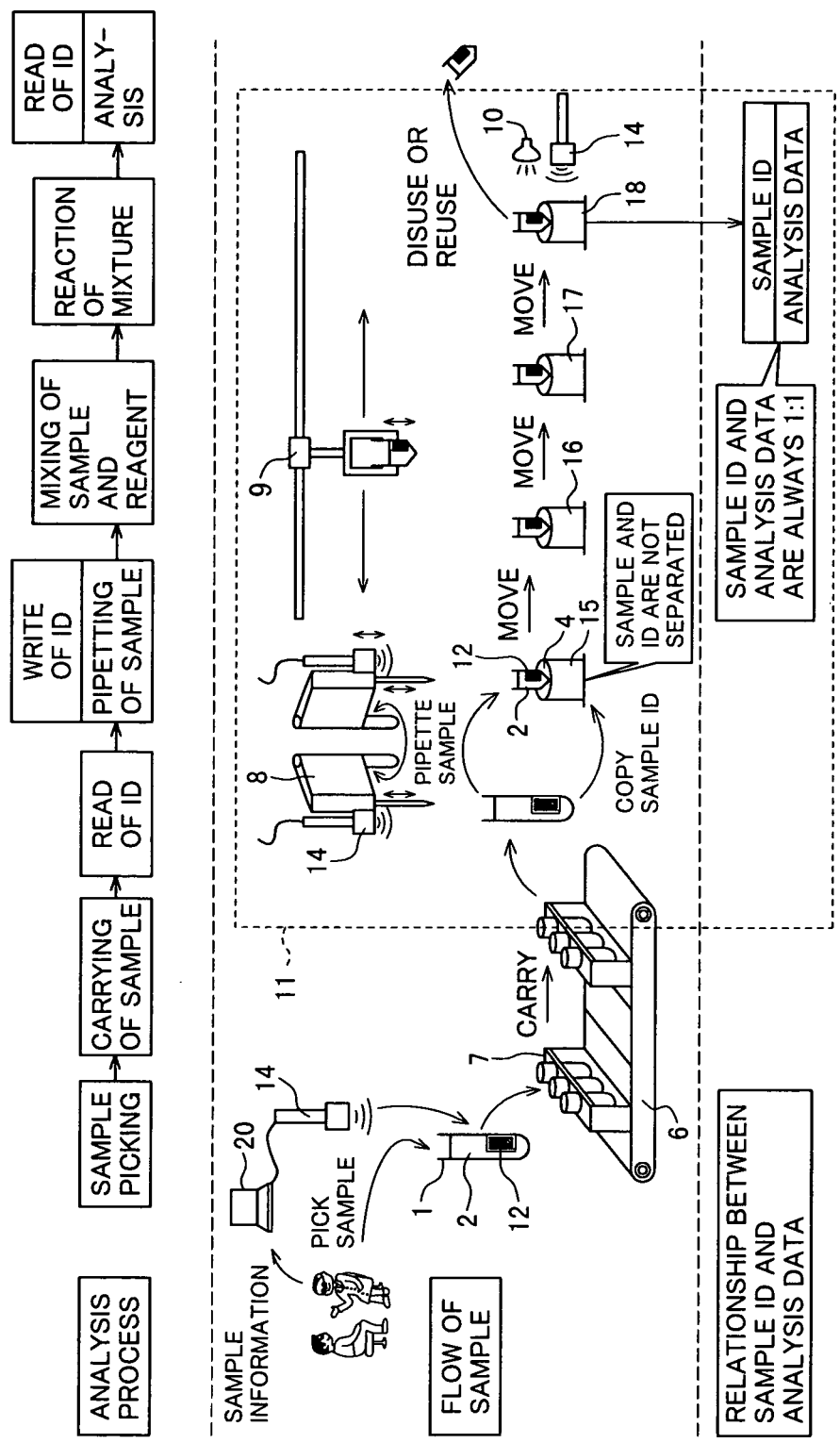
FIG. 1 schematically shows movements of a sample and a flow of data, according to an embodiment of the present invention, in analysis apparatus having a read/write-enable ID carrier provided on a sample container, into which the sample is pipetted, during a process from carrying of the sample into the analysis apparatus to output of an analysis result through successive steps.

For clearer understanding of the present invention, a known apparatus will first be briefly described below with reference to FIG. 3. In the known apparatus for reading a sample ID, while a sample 2 is contained in a sample container 1, the relationship between the sample ID and the sample 2 is physically constant. However, after the sample ID is read by a BCR (barcode reader) 5 and the sample 2 is transferred to an analysis-dedicated small sample container 4, the sample ID and the sample 2 are separated from each other and processed individually. Following the end of analysis, therefore, the sample ID must be merged with a corresponding analysis result. For that reason, complicated software processing is required to execute prediction control for predicting, based on the contents of analysis, the throughput of analysis apparatus 11 and so on, at what point in time the analysis result corresponding to the read sample ID is outputted, and to make correspondence between the sample ID and the sample 2.

That problem is more significant in the analysis apparatus 11 for processing a plurality of samples 2 at the same time. Such an example is shown in FIG. 3. In the example of FIG. 3, a sample ID is read from a barcode 3 attached to the sample container 1 (or a sample rack 7) in which a sample 2-A is contained, and the sample 2-A is pipetted into one analysis-dedicated small sample container 4 (such as a tube or a palette). After the pipetting of the sample 2-A, a sample ID of a sample 2-B is likewise read and the sample 2-B is pipetted into another analysis-dedicated small sample container 4. In parallel, succeeding analysis steps for the sample 2-A is continued. Then, the sample 2-B is also subjected to similar succeeding analysis steps in a following relation to the sample 2-A. When the contents of analysis and the analysis time are the same for both the sample 2-A and the sample 2-B, the analysis process of the sample 2-A from which the sample ID has been read earlier than the sample 2-B is completed at an earlier point in time, and an analysis result of the sample 2-A is outputted relatively early. On the other hand, the sample ID of the sample 2-A and the sample ID of the sample 2-B are both present in a sample ID table prepared in the analysis apparatus 11 to store the sample ID's. In order to properly merge analysis data A and the corresponding sample ID-A, therefore, it is required to keep the ID reading sequence and the analysis sequence unchanged and to merge the analysis data with the sample ID on the time serial basis.

Figure 3:
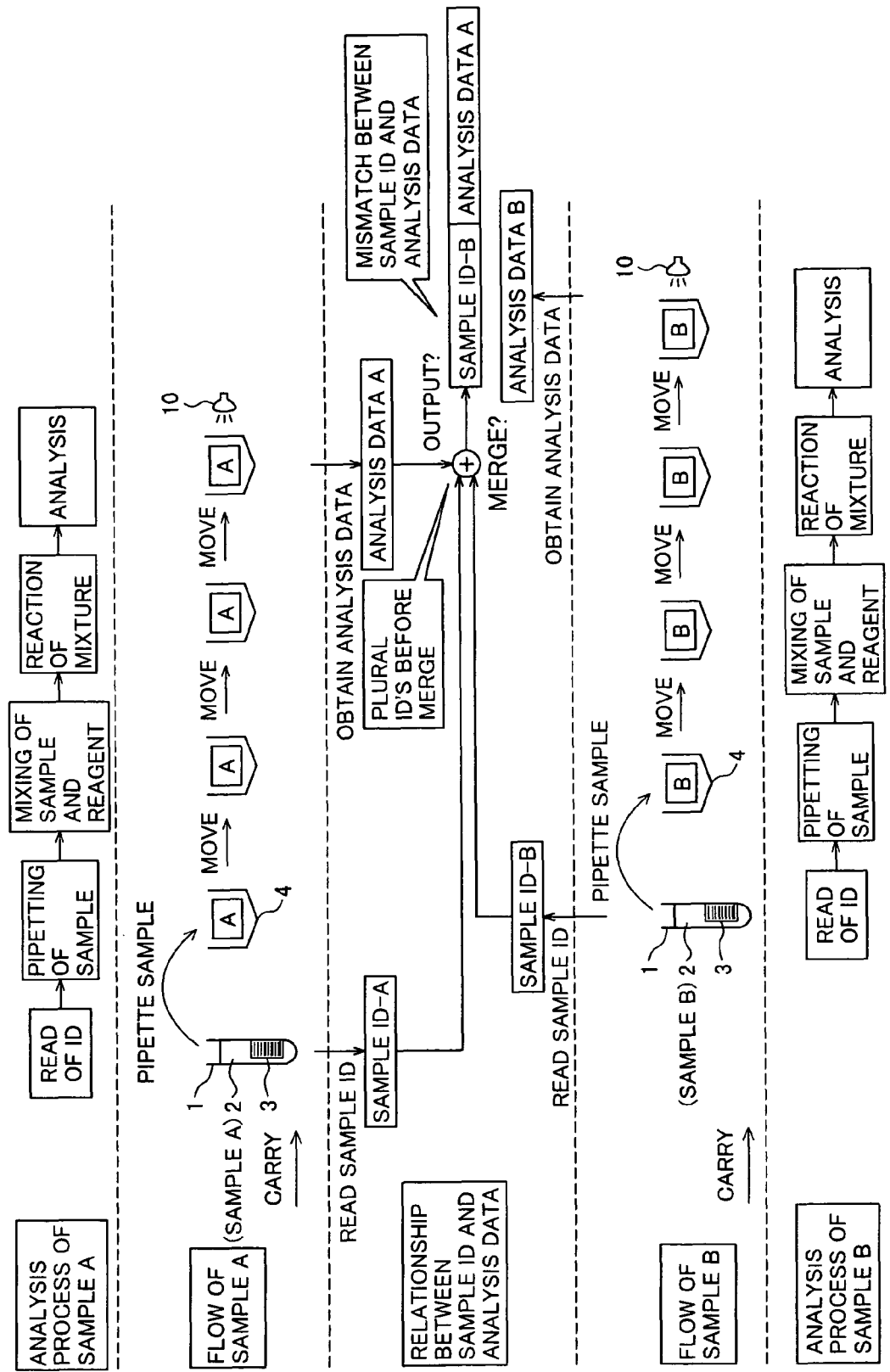
FIG. 3 schematically shows a possibility that assurance of sample identification deteriorates in the known analysis apparatus when a plurality of samples are processed at the same time.
Figure 4:
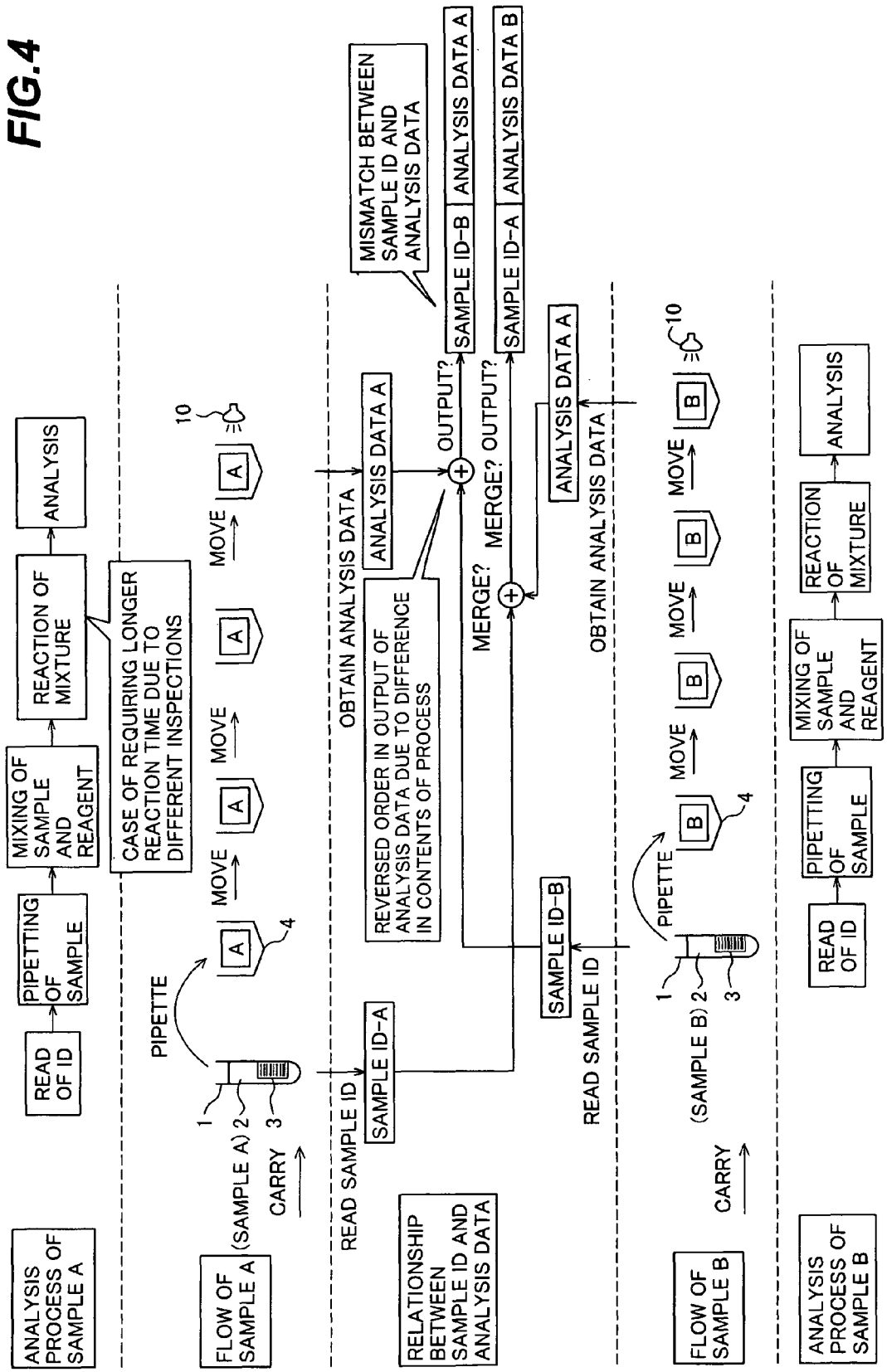
FIG. 4 schematically shows a possibility that assurance of sample identification deteriorates in the known analysis apparatus when a plurality of samples are processed at the same time and the contents of sample analysis and the time required for the analysis process differ from each other.

While FIG. 3 represents the case in which the contents of analysis and the time required for the analysis are the same for a plurality of samples 2, the process is more complicated when the contents of analysis and the time required for the analysis differ for each of the plurality of samples 2. As in the case of FIG. 3, the sample ID of the sample 2-A is read and the sample 2-A is pipetted into one analysis-dedicated small sample container 4. After the pipetting of the sample 2-A, the sample ID of the sample 2-B is likewise read and the sample 2-B is pipetted into another analysis-dedicated small sample container 4. In parallel, succeeding analysis steps for the sample 2-A is continued. However, when the sample 2-A requires a longer reaction time than the sample 2-B as shown in FIG. 4, the analysis process of the sample 2-B from which the sample ID has been read later than the sample 2-A is completed earlier than the completion of analysis of the sample 2-A, and an analysis result of the sample 2-B is outputted at an earlier point in time. In such a case, if the sample ID and the analysis data are merged with each other on the time serial basis as shown in FIG. 4, a mismatch combination of the sample ID and the analysis result occurs. For that reason, management of the process time, prediction control, etc. are required for each sample so that a proper combination of the sample ID and the analysis result is ensured.

In view of those situations, the present invention is featured in having means for, when a pipetting mechanism pipettes a sample from a first sample container (sample container) into a second sample container (analysis-dedicated small sample container), copying at least a part of information recorded in an information recording medium provided on the first sample container into an information recording medium provided on the second sample container.

Embodiments of the present invention will be described below with reference to the drawings. FIG. 1 schematically shows movements of a sample 2 and a flow of data, according to one embodiment of the present invention during a process from carrying of the sample 2 into analysis apparatus 11 to output of an analysis result through successive steps.

In this embodiment, the analysis apparatus 11 includes, as sample containing means, a sample container 1 in the form of a test tube or a sample rack 7 for containing a sample (specimen material) 2, e.g., blood or urine, picked from a patient, and an analysis-dedicated small sample container 4 in the form of a tube or a palette for containing a part of the sample 2 distributively picked out for analysis in the analysis apparatus 11. A main body of the analysis apparatus 11 comprises a carrying mechanism 6, such as a conveyor or a cylinder, for carrying the sample container 1 containing the sample 2 from the outside, a pipette 8 serving as means for distributively injecting the sample 2 from the sample container 1 into the analysis-dedicated small sample container 4, per-step container holding tanks 15 to 18 for holding the analysis-dedicated small sample containers 4 to perform successive analysis steps, such as pipetting (distribution injection), mixing, reaction and analysis, for the sample 2 in the analysis apparatus 11, and a transportation mechanism 9, such as a conveyor or a manipulator, for moving the analysis-dedicated small sample container 4 to the per-step container holding tanks 15 to 18 in a successive way. These components are controlled by a controller unit (not shown). Further, in this embodiment, the sample container 1 and the analysis-dedicated small sample container 4 are each provided with a read/write-enable ID carrier 12 for storing information regarding the sample ID of the sample 2 and the analysis, while the main body of the analysis apparatus 11 includes an ID reader/writer 14 as means for reading and writing the information, such as the sample ID, from and in the read/write-enable ID carrier 12.

Figure 2:
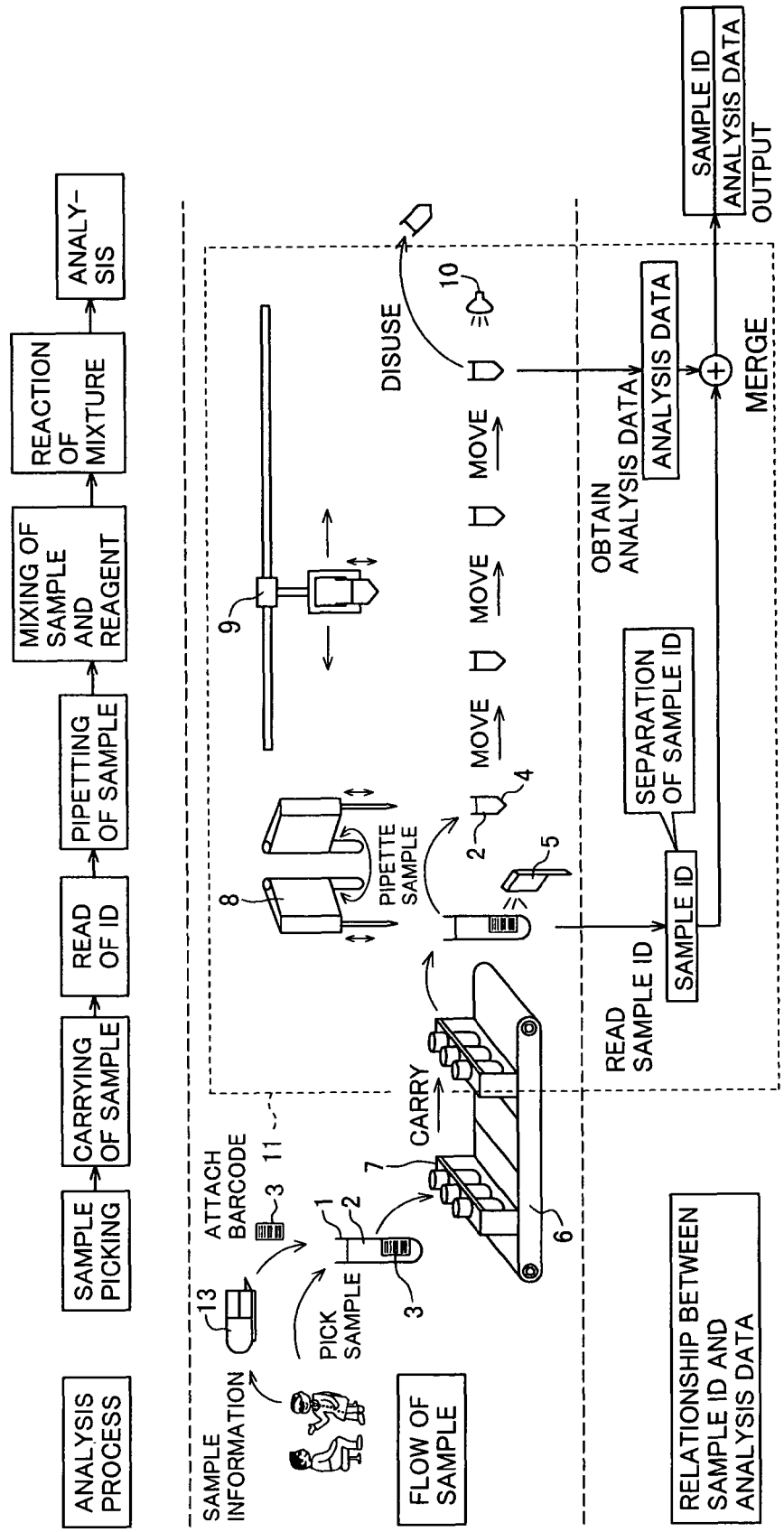
FIG. 2 schematically shows movements of a sample and a flow of data in known analysis apparatus during a process from carrying of the sample into the analysis apparatus to output of an analysis result through successive steps.
Figure 5:
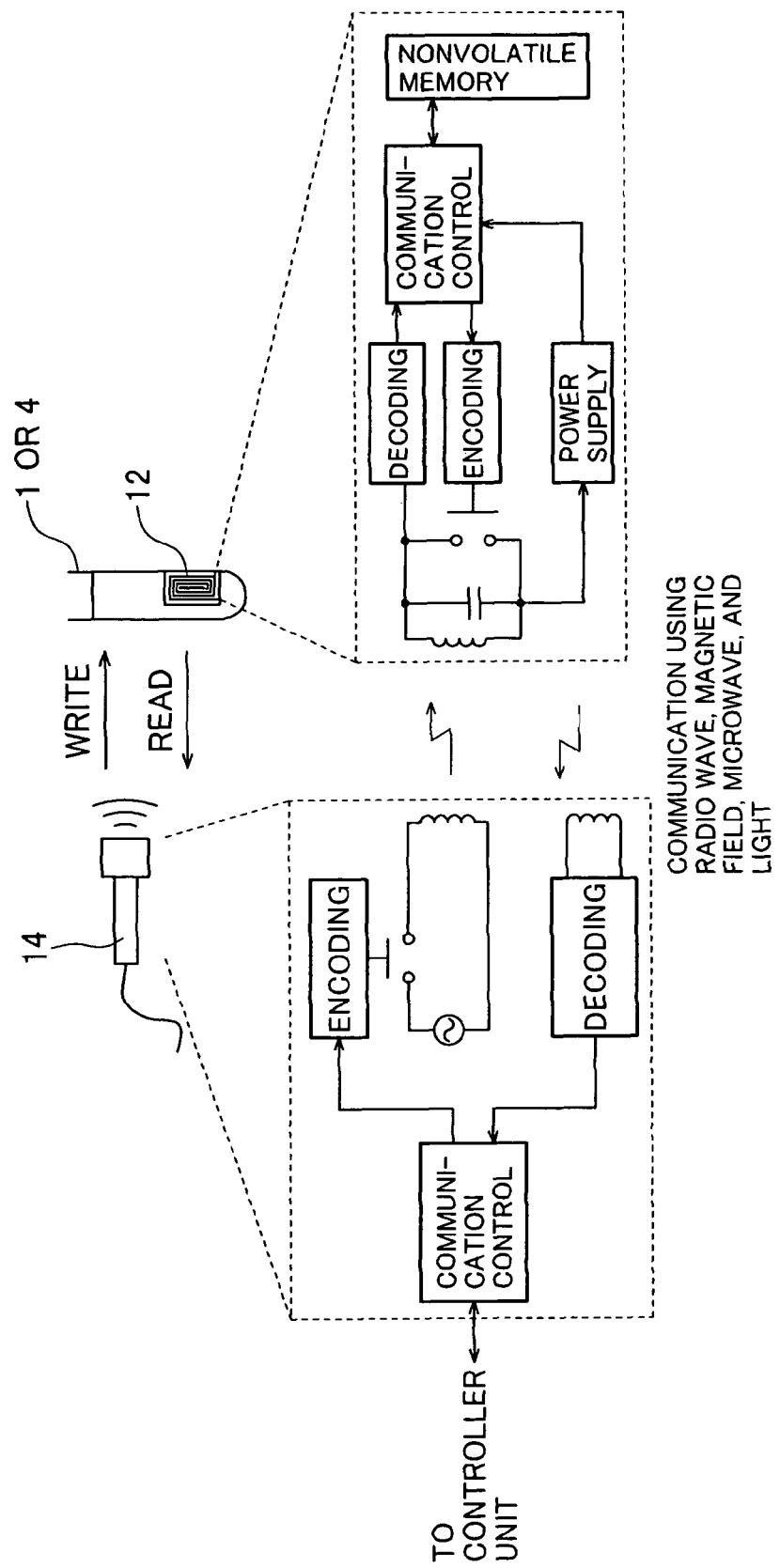
FIG. 5 shows an internal construction of a radio ID tag and a data read/write method.
Figure 6:
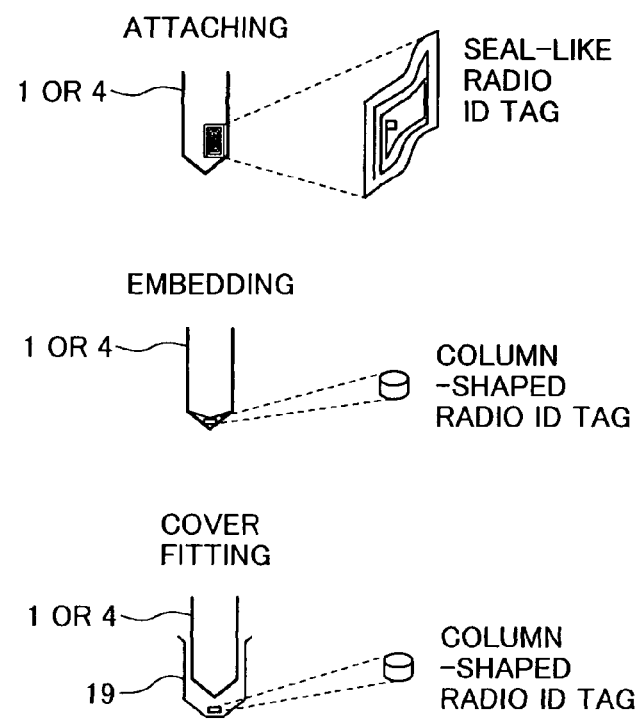
FIG. 6 shows methods for equipping a sample container or an analysis-dedicated small sample container with the read/write-enable ID carrier.

The sample container 1 serving as one of the sample containing means in this embodiment is used to contain blood or urine picked from a patient and is generally in the form of a test tube as shown in FIG. 1. Attached to the test tube is the read/write-enable ID carrier 12, such as a barcode 3 (see FIG. 2), a two-dimensional code, or a radio ID tag, for holding therein the sample ID as an individual identification code of the sample 2 contained in the test tube. In the case of the read/write-enable ID carrier 12 being the barcode 3 or the two-dimensional code, it can be directly attached to the sample container 1. Because a seal-like radio ID tag is commercially available at present, the radio ID tag can also be directly attached to the sample container 1 by using such a seal-like one. Further, as shown in FIG. 5, data in the radio ID tag is rewritable while the radio ID tag is kept in the attached state. In other words, internal information of the radio ID tag can be updated by rewriting with no need of attaching or attaching a new radio ID tag unlike the case of using the barcode 3. Accordingly, the radio ID tag may be embedded in the sample container 1 itself as shown in FIG. 6. As an alternative, when the radio ID tag cannot be directly attached to the sample container 1 due to the problem of, e.g., cost efficiency, a cover 19 may be fitted to the sample container 1 with the radio ID tag disposed between the sample container 1 and the cover 19. This modification enables the sample container 1 to be equipped with the radio ID tag even when the radio ID tag cannot be directly attached to the sample container 1. This modification is further advantageous in points of cost and maintenance because the radio ID tag can be transferred for reuse to another new sample container even if the sample container 1 is broken.

When many samples 2 must be carried into the analysis apparatus 11 at a time, a plurality of sample containers 1 are often put in the sample rack 7 and carried into the analysis apparatus 11 together. In such a case, by equipping the sample rack 7 with the read/write-enable ID carrier 12, those many samples 2 can be managed as a group and the time required for reading the sample ID can be cut.

Figure 7:
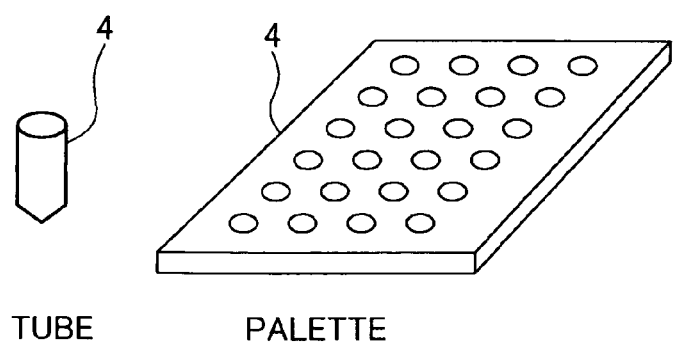
FIG. 7 shows a tube and a palette generally used as the analysis-dedicated sample container.

The analysis-dedicated small sample container 4 serving as the other one of the sample containing means in this embodiment is used to contain a pipetted part of the sample 2 when the sample 2 carried into the analysis apparatus 11 from the outside while being put in the sample container 1 is distributively picked out from the sample container 1 in an amount required for the analysis. The sample 2 is mixed with a reagent in the analysis-dedicated small sample container 4 and then analyzed through mixing and reacting steps. The analysis-dedicated small sample container 4 is generally a resin- or plastic-made container in the form of a tube or a palette as shown in FIG. 7, and is smaller and easier to handle than the test tube for convenience in analyzing a large number of samples 2 in the analysis apparatus 11. The palette is formed to have recesses arrayed in a matrix pattern, in which the samples 2 are to be put, so that a large number of samples 2 can be processed at the same time. In this embodiment, similarly to the sample container 1, the read/write-enable ID carrier 12 for holding therein the sample ID as an individual identification code of the contained sample 2 is also attached to the analysis-dedicated small sample container 4. As with the sample container 1, the read/write-enable ID carrier 12 can be attached to the analysis-dedicated small sample container 4 by any of the methods shown in FIG. 6, i.e., attaching, embedding, or a method of fitting the cover 19 to the analysis-dedicated small sample container 4 and placing the read/ write-enable ID carrier 12 between the analysis-dedicated small sample container 4 and the cover 19. The analysis-dedicated small sample container 4 is generally disused after the use unlike the sample container 1, and hence the attaching or embedding method is disadvantageous in point of cost efficiency because the read/write-enable ID carrier 12 is also disused together with the container at the same time as when the latter is disused. In contrast, the method of fitting the cover 19 to the analysis-dedicated small sample container 4 and placing the read/write-enable ID carrier 12 between the analysis-dedicated small sample container 4 and the cover 19 enables the read/write-enable ID carrier 12 to be used again, and hence it is advantageous in point of the cost efficiency. The attaching or embedding method may also be employed when the analysis-dedicated small sample container 4 is used again after cleaning without being disused.

The pipette 8 serves as means for transferring, to the analysis-dedicated small sample container 4, the sample 2 that has been carried into the analysis apparatus 11 while being contained in the sample container 1. The pipette 8 is controlled by the controller unit in the analysis apparatus 11 so as to suck, from the sample container 1, a proper amount of the sample 2 required for the analysis and to release the sucked sample into the analysis-dedicated small sample container 4 in accordance with the sample ID and analysis information, such as the contents of analysis, the analysis steps, and end-of-step flags, which have been read from the read/write-enable ID carrier 12 provided on the sample container 1 by the ID reader/writer 14 described later.

The transportation mechanism 9 serves as means for successively moving the analysis-dedicated small sample container 4 to the per-step container holding tanks 15 to 18 described later, and it is generally constituted by a conveyor or a manipulator. The transportation mechanism 9 is controlled by the controller unit in the analysis apparatus 11 so as to move the analysis-dedicated small sample container 4 from one of the per-step container holding tanks 15 to 18 to another corresponding to the place of the next analysis step in accordance with the sample ID and the analysis information, such as the contents of analysis, the analysis steps, and end-of-step flags, which have been read from the read/write-enable ID carrier 12 provided on the sample container 1 by the ID reader/writer 14 described later.

The ID reader/writer 14 serves as means for reading and writing information, such as the sample ID, from and in the read/write-enable ID carrier 12. When the read/write-enable ID carrier 12 is in the form of the barcode 3 or a two-dimensional code, the barcode reader 5 is used as the ID reader, while a printer called a barcode labeler 13 (FIG. 2) or a two-dimensional code labeler is used as the ID writer. Further, when the read/write-enable ID carrier 12 is in the form of a radio ID tag, the ID reader/writer 14 reads and writes information through an antenna in the radio ID tag by using radio waves as a medium, i.e., by transmitting and receiving radio signals to and from an IC memory in the radio ID tag, as shown in FIG. 5. In that case, therefore, the printer such as the barcode labeler 13 is not required and the reader and the writer can be constituted as one common unit. This embodiment employs the radio ID tag. Regardless of any type of the ID reader/writer 14 being used as the reader or the writer, by positioning the ID reader/writer 14 close to the read/write-enable ID carrier 12, it is possible to read and write data stored in the read/write-enable ID carrier 12, i.e., the information such the sample ID and various items regarding the analysis, via non-contact data communication means using light, magnetism, or radio waves.

In the present invention, read and write of the sample ID from and in the read/write-enable ID carrier 12 are performed at the time when the sample 2 is distributively injected from the sample container 1 into the analysis-dedicated small sample container 4, or/and when the analysis-dedicated small sample container 4 is moved through the per-step container holding tanks 15 to 18, described below, for the successive analysis steps. The pipette 8 and the transportation mechanism 9 are required respectively to have the functions of distributively injecting the sample 2 and moving the analysis-dedicated small sample container 4. For that purpose, the pipette 8 must be moved to come close to the sample container 1 when it sucks the sample 2, and to come close to the analysis-dedicated small sample container 4 when it releases the sample 2. Also, the transportation mechanism 9 must be brought into contact with the analysis-dedicated small sample container 4 to transport the same. Taking into account the above feature, in the present invention, the ID reader/writer 14 is disposed integrally with the pipette 8 or/and the transportation mechanism 9 to perform pipette operation control of the sample 2 and read/write control of the sample ID in one process or/and to perform movement control of the analysis-dedicated small sample container 4 and read/write control of the sample ID in one process. As a result, not only the control process but also the structure of the analysis apparatus 11 can be simplified and a space required for installation of the analysis apparatus 11 can be reduced.

The per-step container holding tanks 15 to 18 serve as means for holding the analysis-dedicated small sample containers 4 to perform successive analysis steps, such as pipetting (distribution injection), mixing, reaction and analysis, for the sample 2 in the analysis apparatus 11. The per-step container holding tanks 15 to 18 are disposed respectively corresponding to the process steps of the analysis, such as pipetting, mixing, reaction and analysis, in some cases. In other cases, several ones of the analysis steps are performed in the same tank. This embodiment is constructed such that a pipetting-step container holding tank 15, a mixing-step container holding tank 16, a reaction-step container holding tank 17, and an analysis-step container holding tank 18 are disposed in a one-to-one relation to the analysis steps of pipetting, mixing, reaction and analysis. Generally, these container holding tanks 15 to 18 each have not only the function of holding the containers, but also the temperature management function, the stirring function, etc.

The carrying mechanism 6 serves as means for carrying the sample container 1 containing the sample 2 from the outside, and it is generally constituted by a conveyor or a cylinder.

The foregoing is the construction (components and mechanisms) necessary for implementing the present invention.

A method of transferring the sample ID in the analysis apparatus 11 according to this embodiment will be described below.

Referring to FIG. 1, the sample 2, e.g., blood or urine, picked from a patient is first poured into the sample container 1 such as a test tube. The sample container 1 includes the read/write-enable ID carrier 12 embedded in it. The read/write-enable ID carrier 12 embedded in the sample container 1 stores the sample ID as an individual identification code of the sample 2 contained in the sample container 1, information necessary for determining the contents of analysis process, such as inspection information, inspection conditions, inspection steps, and end-of-step flags, and, if necessary, information regarding the patient, such as the patient name. Those items of information are written by the ID reader/ writer 14 into the read/write-enable ID carrier 12 of the sample container 1 at the time when the sample 2 is picked from the patient.

Figure 8:
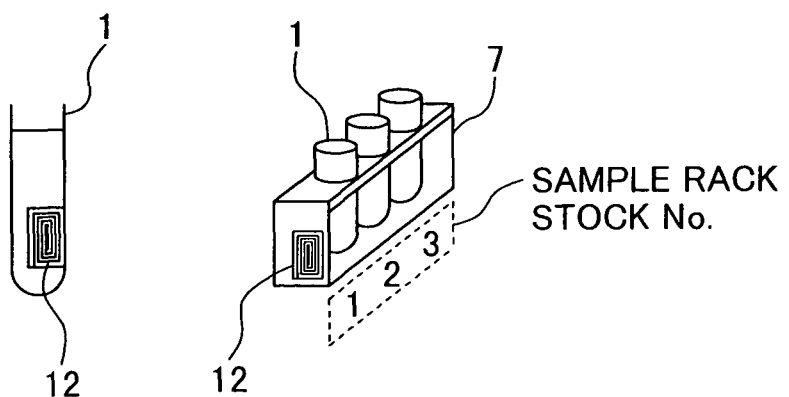
FIG. 8 shows a group management method for sample and sample ID's by using a sample rack and a read/write-enable ID carrier provided on the sample rack.

To transport a plurality of samples 2 to the analysis apparatus 11 at the same time, a plurality of sample containers 1 are often placed in the sample rack 7 and carried together into the analysis apparatus 11 by transporting the sample rack 7. In such a case, instead of providing the read/write-enable ID carrier 12 on the sample container 1 as shown on the left side of FIG. 8, the read/write-enable ID carrier 12 is provided on the sample rack 7 as shown on the right side of FIG. 8 so that the plurality of samples 2 are managed as a group for each sample rack 7. The read/write-enable ID carrier 12 provided on the sample rack 7 stores what sample 2 is placed in which one of spaces of the sample rack 7 for the group management.

The sample container 1 or the sample rack 7 including the sample containers 1 placed therein is carried into the analysis apparatus 11 by the carrying mechanism 6. Generally, the carrying mechanism 6 is constituted as a cylinder when the sample container 1 in the form of a test tube is carried, and as a conveyor when the sample rack 7 is carried.

After the sample container 1 or the sample rack 7 including the sample containers 1 placed therein has been carried, the analysis apparatus 11 starts the analysis process. First, from the read/write-enable ID carrier 12 provided on the sample container 1 or the sample rack 7, the sample ID of the carried sample 2 and the analysis information, such as inspection information, inspection conditions, inspection steps, and end-of-step flags, are read by the ID reader/writer 14 to determine to whom the carried sample 2 belongs, what kind of inspection is required, and what kind of analysis is required for the inspection. Based on such information, the controller unit in the analysis apparatus 11 controls the pipette 8 so as to suck a proper amount of the sample 2 from the sample container 1 and to release the sucked sample 2 into the analysis-dedicated small sample container 4 that has been set beforehand in the pipetting-step container holding tank 15 within the analysis apparatus 11.

At the time of releasing the sucked sample 2 into the analysis-dedicated small sample container 4, the sample ID and the analysis information both read from the read/write-enable ID carrier 12 provided on the sample container 1 at the time of sucking the sample 2 are written by the ID reader/writer 14 into the read/write-enable ID carrier 12 provided on the analysis-dedicated small sample container 4.

Figure 9:
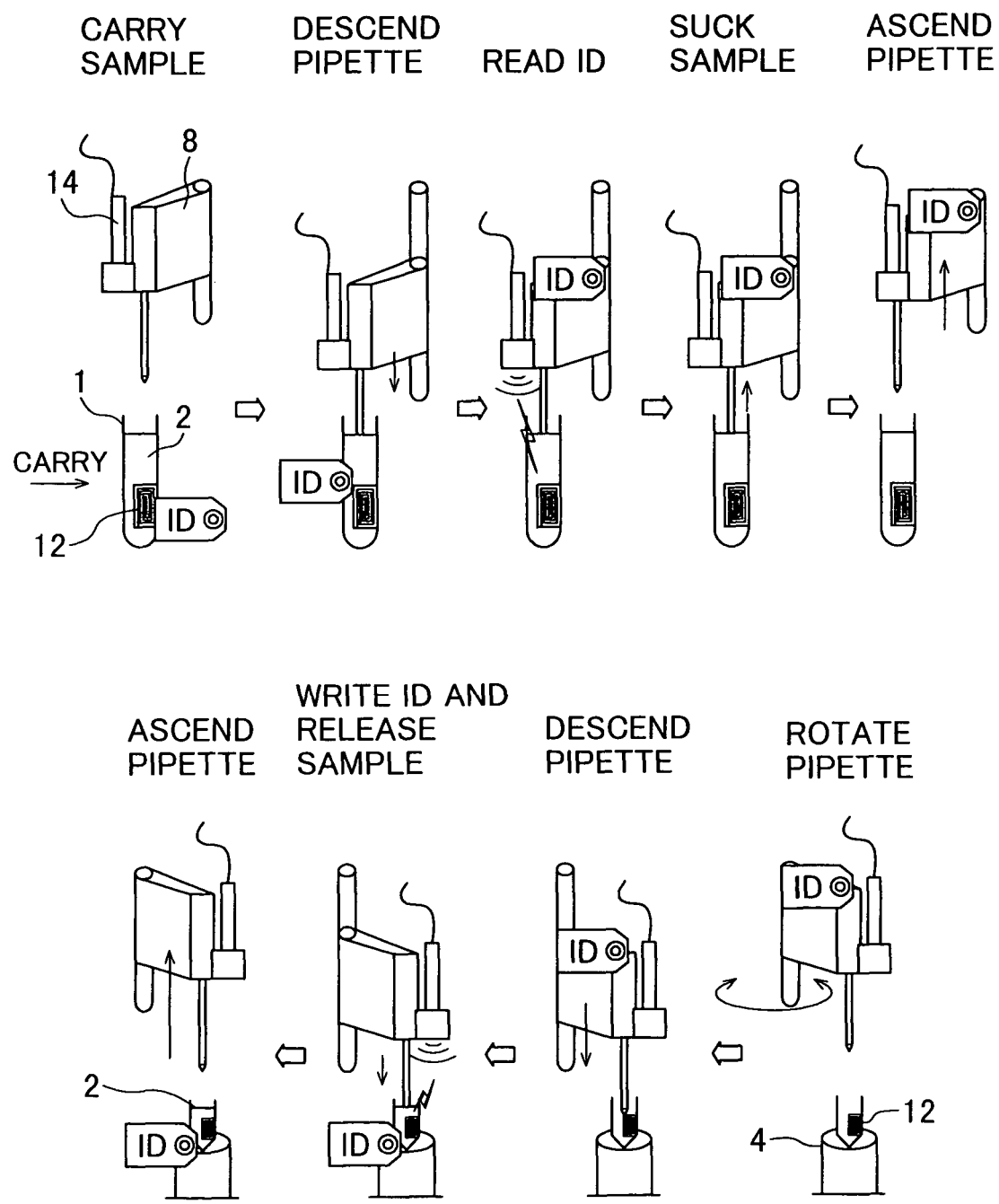
FIG. 9 shows a simultaneous transfer method for a sample and a sample ID by using a pipette and an ID reader/writer provided on the pipette.

In this embodiment, read and write of the sample ID from and in the read/write-enable ID carrier 12 are performed at the time when the sample 2 is distributively injected from the sample container 1 into the analysis-dedicated small sample container 4. As mentioned above, the pipette 8 is used for the distribution injection of the sample 2. For that purpose, the pipette 8 must be moved to come close to the sample container 1 when it sucks the sample 2, and to come close to the analysis-dedicated small sample container 4 when it releases the sample 2. Also, read and write of the sample ID and the analysis information from and in the read/write-enable ID carrier 12 are performed using the ID reader/writer 14. For that purpose, the ID reader/writer 14 must be moved to come close to the read/write-enable ID carrier 12 provided on the sample container 1 or the analysis-dedicated small sample container 4. Taking into account the above feature, in this embodiment, the ID reader/writer 14 is disposed integrally with each of the pipette 8 and the transportation mechanism 9. With such an integral construction, as shown in FIG. 9, at the same time when the pipette 8 is moved to come close to the sample container 1 when it sucks the sample 2 from the sample container 1, the ID reader/writer 14 integral with the pipette 8 reads the sample ID and the analysis information from the read/write-enable ID carrier 12 provided on the sample container 1. Further, at the same time when the pipette 8 releases the sucked sample 2 into the analysis-dedicated small sample container 4, the ID reader/writer 14 integral with the pipette 8 writes the sample ID and the analysis information, which have been read in the above step, in the read/write-enable ID carrier 12 provided on the analysis-dedicated small sample container 4. Thus, the pipette operation control for the sample 2 and the read/write control of the sample ID are integrated, while the control of the transportation mechanism 9 for moving the analysis-dedicated small sample container 4 and the read/write control of the sample ID are integrated. As a result, not only the control process but also the structure of the analysis apparatus 11 can be simplified and a space required for installation of the analysis apparatus 11 can be reduced. Further, because the ID reader/writer 14 is directed toward the sample container 1 as a target of the sample sucking or the analysis-dedicated small sample container 4 as a target of the sample releasing whenever each of different samples 2 is sucked and released, the read and the write can be reliably performed to avoid, e.g., an error that the read sample ID is in fact an erroneous ID read from the read/write-enable ID carrier 12 provided on the sample container 1 adjacent to the corresponding one.

In the embodiment shown in FIG. 1, the subsequent mixing and reaction steps are performed in the same analysis-dedicated small sample container 4, and hence read of the sample ID from the read/write-enable ID carrier 12 is not needed any more after the pipetting of the sample. In a final analysis step of outputting an analysis result, the sample ID and the analysis information are read again from the read/write-enable ID carrier 12 provided on the analysis-dedicated small sample container 4. The sample ID read from the read/write-enable ID carrier 12 provided on the analysis-dedicated small sample container 4, which has been subjected to the analysis process, is merged with the analysis data obtained in the analysis process. Merged data is then outputted as the analysis result.

By employing the method described above, since each sample 2 in the analysis apparatus 11 and the sample ID as an individual identification code of the relevant sample 2 are always held in a physically combined state, a possibility of the sequence in read of the sample ID being mismatched with the sequence in output of the analysis result is eliminated even when a plurality of samples are processed at the same time. Further, since the output of the analysis data and the read of the sample ID are performed at the same timing from the same container, the combination of the sample ID and the analysis data is surely prevented from being brought into an improper state, and assurance of sample identification can be increased. Moreover, since the sample ID read at the time of completion of the analysis always represents the ID of the sample for which the analysis has been completed at that time, the required software processing is simple and hence complicated processing, such as prediction control, is no longer required even when the number of the samples 2 to be processed at the same time or processed in different ways is increased.

Figure 10:
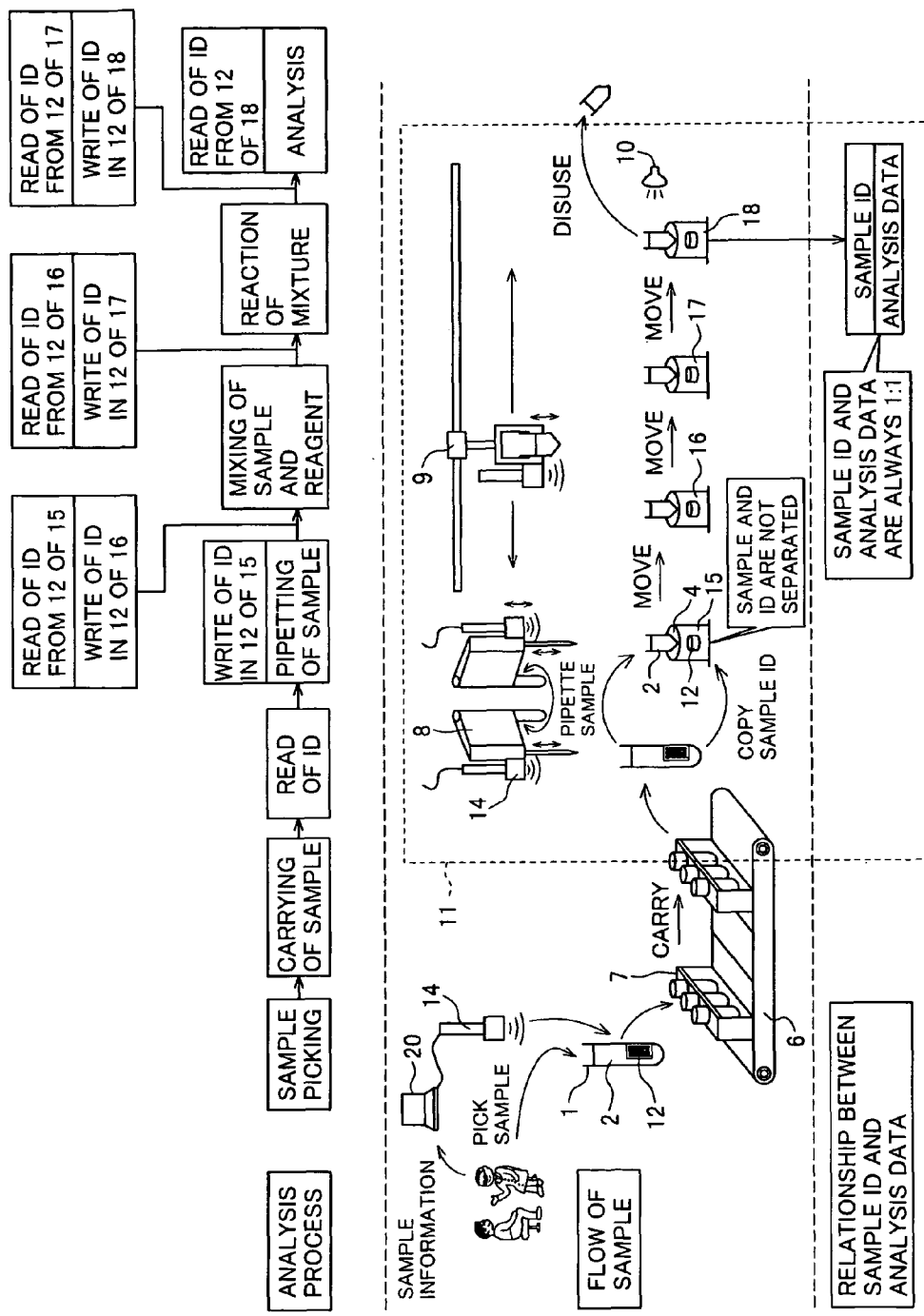
FIG. 10 schematically shows movements of a sample and a flow of data, according to an expanded version of the embodiment shown in FIG. 1, in analysis apparatus having a read/write-enable ID carrier provided on a container holding tank disposed in each step for holding the analysis-dedicated small sample container, during a process from carrying of the sample into the analysis apparatus to output of an analysis result through successive steps.

FIG. 10 schematically shows an expanded version of the embodiment shown in FIG. 1. The embodiment of FIG. 10 represents analysis apparatus having the read/write-enable ID carrier 12 provided on each of the pipetting-step container holding tank 15, the mixing-step container holding tank 16, the reaction-step container holding tank 17, and the analysis-step container holding tank 18, which are disposed in a one-to-one relation to the analysis steps, instead of providing the read/write-enable ID carrier 12 on the analysis-dedicated small sample container 4. A method of transferring the sample ID in the analysis apparatus 11 will be described below with reference to FIG. 10.

Referring to FIG. 10, the sample 2, e.g., blood or urine, picked from a patient is first poured into the sample container 1 such as a test tube. The sample container 1 includes the read/write-enable ID carrier 12 embedded in it. The read/write-enable ID carrier 12 embedded in the sample container 1 stores the sample ID as an individual identification code of the sample 2 contained in the sample container 1, the analysis information, and so on. Those items of information are written by the ID reader/writer 14 into the read/write-enable ID carrier 12 embedded in the sample container 1 at the time when the sample 2 is picked from the patient.

The sample container 1 or the sample rack 7 including the sample containers 1 placed therein is carried into the analysis apparatus 11 by the carrying mechanism 6. As in the embodiment described above, the carrying mechanism 6 is constituted as a cylinder when the sample container 1 in the form of a test tube is carried, and as a conveyor when the sample rack 7 is carried.

After the sample container 1 or the sample rack 7 including the sample containers 1 placed therein has been carried, the analysis apparatus 11 starts the analysis process. First, from the read/write-enable ID carrier 12 provided on the sample container 1 or the sample rack 7, the sample ID of the carried sample 2 and the analysis information, such as inspection information, inspection conditions, inspection steps, and end-of-step flags, are read by the ID reader/writer 14 to determine to whom the carried sample 2 belongs, what kind of inspection is required, and what kind of analysis is required for the inspection. Based on such information, the controller unit in the analysis apparatus 11 controls the pipette 8 so as to suck a proper amount of the sample 2 from the sample container 1 and to release the sucked sample 2 into the analysis-dedicated small sample container 4 that has been set beforehand in the pipetting-step container holding tank 15 within the analysis apparatus 11.

At the time of releasing the sucked sample 2 into the analysis-dedicated small sample container 4, the sample ID and the analysis information both read from the read/write-enable ID carrier 12 provided on the sample container 1 at the time of sucking the sample 2 are written by the ID reader/writer 14, which is provided on the pipette 8, into the read/write-enable ID carrier 12 provided on the pipetting-step container holding tank 15 holding the analysis-dedicated small sample container 4 into which the sample is released.

Figure 11:
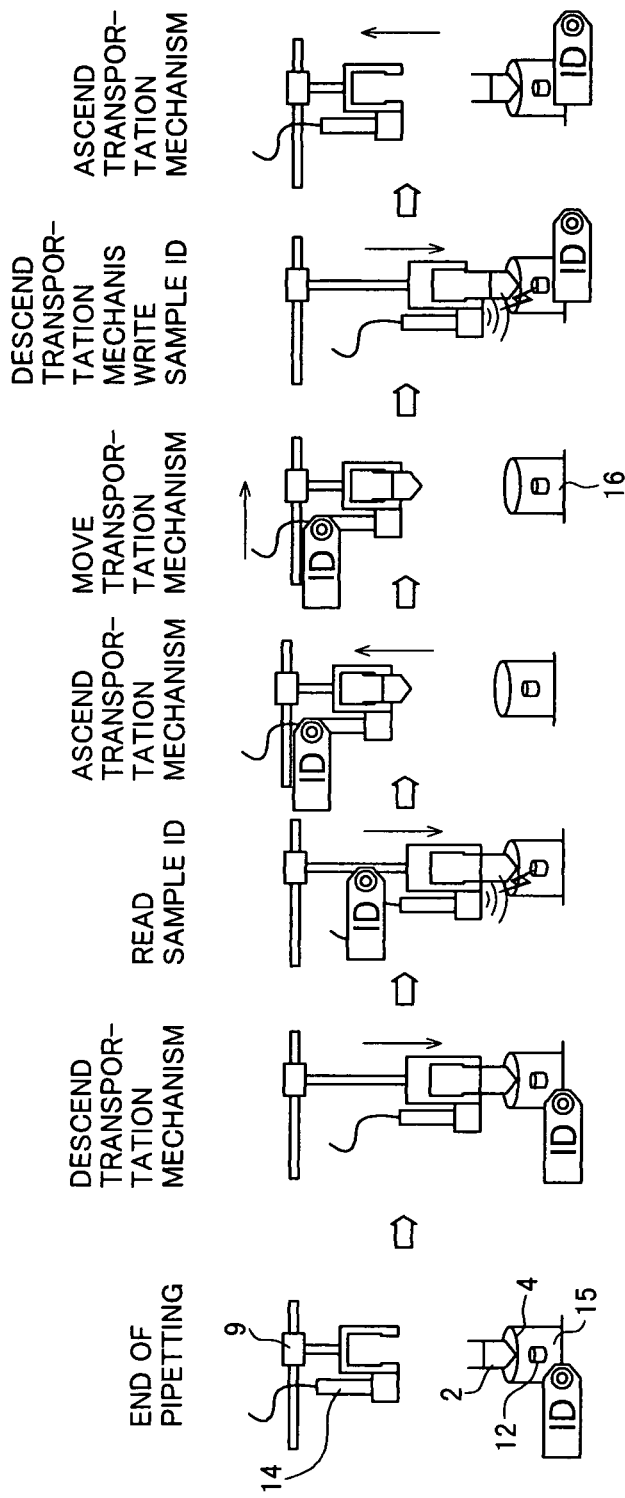
FIG. 11 shows a simultaneous transfer method for a sample and a sample ID by using a transportation mechanism and an ID reader/writer provided on the transportation mechanism.
Figure 12:
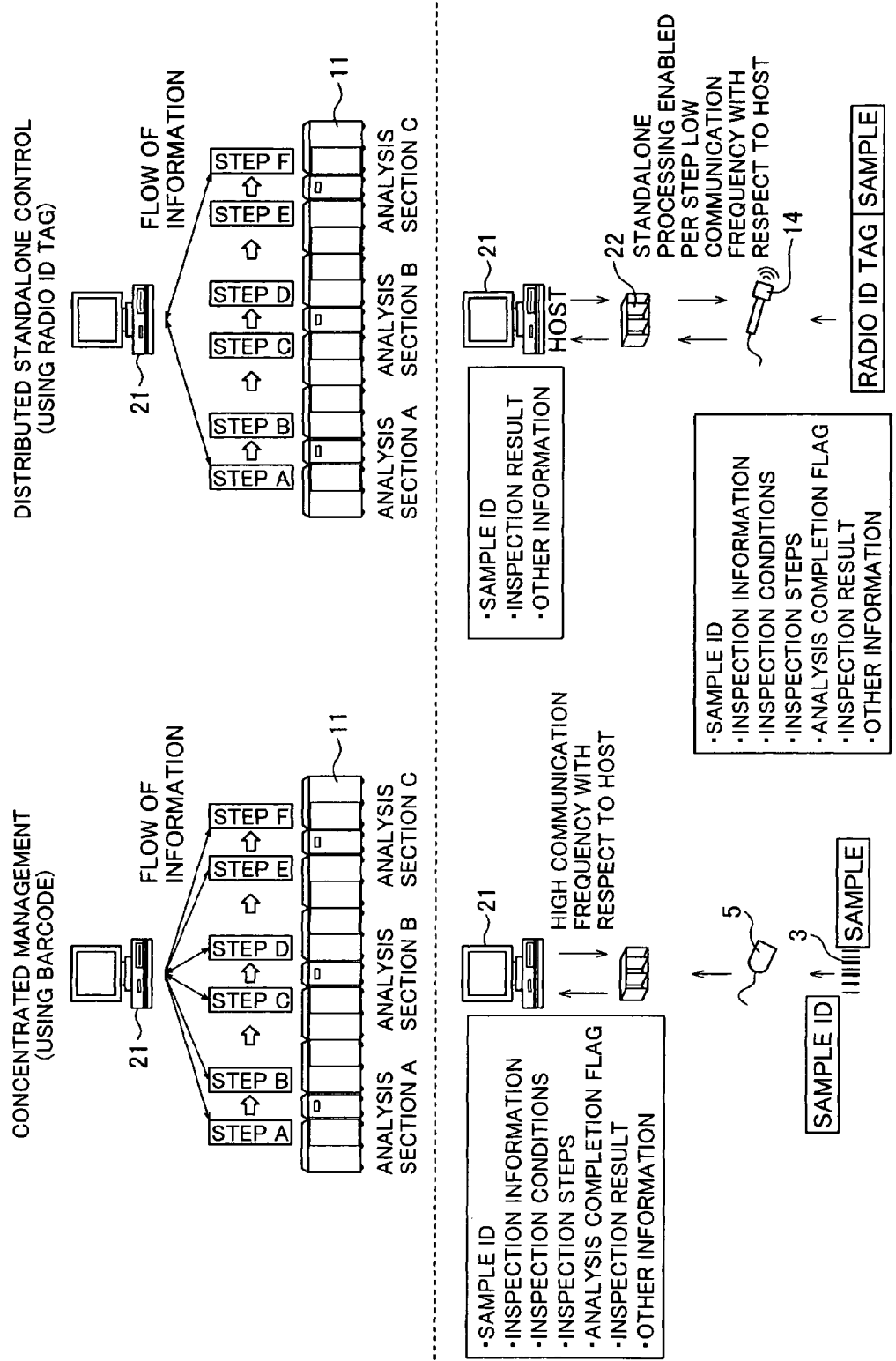
FIG. 12 shows that a burden imposed on a host can be reduced by storing, in the ID carrier, materials for determining the analysis process.

Subsequently, to mix a reagent with the sample 2, the analysis-dedicated small sample container 4 containing the sample 2 to be analyzed is moved to the mixing-step container holding tank 16 by the transportation mechanism 9. The transportation mechanism 9 serves as means for successively moving the analysis-dedicated small sample container 4 to the per-step container holding tanks 15 to 18, and it is generally constituted by a conveyor or a manipulator. The transportation mechanism 9 is controlled by the controller unit in the analysis apparatus 11 so as to move the analysis-dedicated small sample container 4 from one of the per-step container holding tanks 15 to 18 to another corresponding to the place of the next analysis step in accordance with the sample ID and the analysis information, such as the contents of analysis, the analysis steps, and end-of-step flags, which have been read from the read/write-enable ID carrier 12 by the ID reader/writer 14. In this embodiment, like the pipette 8, the transportation mechanism 9 is also equipped integrally with the ID reader/writer 14. Accordingly, as shown in FIG. 11, at the time when the transportation mechanism 9 comes close to the analysis-dedicated small sample container 4 to move it, the ID reader/writer 14 provided on the transportation mechanism 9 reads the sample ID and the analysis information regarding the sample 2, which is contained in the analysis-dedicated small sample container 4 held in the pipetting-step container holding tank 15, from the read/write-enable ID carrier 12 provided on the pipetting-step container holding tank 15 holding the analysis-dedicated small sample container 4 at that time. Thereafter, at the same time when the transportation mechanism 9 transports the analysis-dedicated small sample container 4 and comes close to the mixing-step container holding tank 16 as a next container holding tank, the ID reader/writer 14 provided on the transportation mechanism 9 writes the sample ID and the analysis information, which have been read in the above step from the read/write-enable ID carrier 12 provided on the pipetting-step container holding tank 15, into the read/write-enable ID carrier 12 provided on the mixing-step container holding tank 16. The analysis-dedicated small sample container 4 transported by the transportation mechanism 9 is then held in the mixing-step container holding tank 16. Subsequently, whenever the analysis-dedicated small sample container 4 is transported from the mixing-step container holding tank 16 to the reaction-step container holding tank 17, and then from the reaction-step container holding tank 17 to the analysis-step container holding tank 18 to perform the subsequent steps of mixing, reaction and analysis, the sample ID and the analysis information are transferred in a similar manner. Finally, when the analysis is completed in the analysis-step container holding tank 18 and analysis data is outputted, the sample ID and the analysis information are read by the ID reader/writer 14 from the read/write-enable ID carrier 12 provided on the analysis-step container holding tank 18 and are merged with the obtained analysis data. Merged data is then outputted as the analysis result. With the embodiment shown in FIG. 10, since the transportation mechanism 9 is equipped with the ID reader/writer 14, when the analysis-dedicated small sample container 4 is removed from the analysis-step container holding tank 18 after the completion of the analysis, the ID reader/writer 14 provided on the transportation mechanism 9 reads the sample ID from the read/write-enable ID carrier 12 provided on the analysis-step container holding tank 18 and presents the read sample ID as the sample ID for the analysis data outputted at that time. The above-described method is advantageous in that since read of the sample ID at the time of completion of the analysis is made by the ID reader/writer 14 provided on the transportation mechanism 9, there is no need of separately providing the ID reader/writer 14 for reading the sample ID when the analysis result is outputted, and hence the number of the ID readers/writers 14 required can be minimized.

By employing the method described above, as in the case of equipping the analysis-dedicated small sample container 4 with the read/write-enable ID carrier 12, since the sample 2 and the sample ID are always held in a physically combined state, a possibility of the sequence in read of the sample ID being mismatched with the sequence in output of the analysis result is eliminated even when a plurality of samples 2 are processed at the same time. Further, since the output of the analysis data and the read of the sample ID are performed at the same timing from the same container, the combination of the sample ID and the analysis data is surely prevented from being brought into an improper state, and assurance of sample identification can be increased. Moreover, since the sample ID read at the time of completion of the analysis always represents the ID of the sample 2 for which the analysis has been completed at that time, the required software processing is simple and hence complicated processing, such as prediction control, is no longer required even when the number of the samples 2 to be processed at the same time or processed in different ways is increased.

This embodiment differs from the case of equipping the analysis-dedicated small sample container 4 with the read/write-enable ID carrier 12 in that, since the read/write-enable ID carrier 12 is provided on each of the per-step container holding tanks 15 to 18 fixedly installed in the analysis apparatus 11 instead of providing the read/write-enable ID carrier 12 on the analysis-dedicated small sample container 4 which is usually disused after one use, the number of the read/write-enable ID carriers 12 used can be reduced and the cost can be cut as compared with the case of equipping the analysis-dedicated small sample container 4 with the read/write-enable ID carrier 12.

The present invention has the following advantages. Since each sample in the analysis apparatus and the sample ID as an individual identification code of the relevant sample are always held in a physically combined state, a possibility of the sequence in read of the sample ID being mismatched with the sequence in output of the analysis result is eliminated even when a plurality of samples are processed at the same time. Further, since each pair of the sample ID and the sample 2 are held in a physically combined state until the end of the analysis process and the output of the analysis data and the read of the sample ID are performed at the same timing from the same container, the combination of the sample ID and the analysis data is surely prevented from being brought into an improper state, and assurance of sample identification can be increased. Moreover, since the sample ID read at the time of completion of the analysis always represents the ID of the sample for which the analysis has been completed at that time, the required software processing is simple and hence complicated processing, such as prediction control, is no longer required even when the number of samples to be processed at the same time or processed in different ways is increased.

Also, by providing the read/write-enable ID carrier not on the analysis-dedicated small sample container, but on each of the per-step container holding tanks for holding the analysis-dedicated small sample containers to perform the respective steps of the analysis, assurance of sample identification can be increased as in the case of providing the read/write-enable ID carrier on the analysis-dedicated small sample container. In addition, since the read/write-enable ID carrier is provided on each of the per-step container holding tanks fixedly installed in the analysis apparatus instead of providing the read/write-enable ID carrier on the analysis-dedicated small sample container which is usually disused after one use, the number of the read/write-enable ID carriers used can be reduced and the cost can be cut as compared with the case of equipping the analysis-dedicated small sample container with the read/write-enable ID carrier.

Furthermore, when a radio ID tag or a two-dimensional code having a larger data storage capacity than a barcode is used as the read/write-enable ID carrier, various additional items of information (such as the sample (blood) taking date, the patient name, the contents of analysis required for the sample, information regarding the analysis process (recipe), and the analysis result) can also be recorded in the read/write-enable ID carrier, i.e., on the ID label side where only the information of the sample ID has been recorded in the past. In the conventional case of recording only the sample ID in the barcode, information necessary for executing the analysis must be inquired to the host computer based on the read sample ID whenever occasion demands. In contrast, in the analysis apparatus of the present invention wherein the various additional items of information are recorded on the sample side and the sample ID and the process information regarding the relevant sample are read from the read/write-enable ID carrier prior to each of the analysis steps, an inquiry to the host computer is just required at the start and end of the analysis process, and each analysis step can be performed in a standalone processing manner. It is therefore possible to reduce communication frequency with respect to the host computer and to lessen the carry of the host computer.

What is claimed is:

1. An automatic analyzer comprising:
   a first sample container for containing a sample;
   a first information recording medium provided on said first sample container and recording information regarding the sample contained in said first sample container and inspection conditions necessary for determining the contents of the analysis process;
   a second sample container for containing a second sample dispensed from said first sample container;
   a pipetting mechanism for dispensing the second sample from said first sample container into the second sample container;
   a plurality of container holding tanks in an analysis portion of said automatic analyzer, each of said container holding tanks holding said second sample container at a process step portion of said automatic analyzer;
   a second information recording medium provided on each of said container holding tanks, said second information recording medium recording information regarding the second sample contained in said second sample container and inspection conditions necessary for determining the contents of the analysis process, the information being recorded on said second information recording medium being recorded with out contacting said second information recording medium;
   a transportation mechanism for transporting said second sample container from a first container holding tank to each of the other container holding tanks
   a fist information reader/writer for copying at least a part of information regarding the sample contained in said first sample container into said second information recording medium at the time of a dispensing operation of said pipetting mechanism to dispense the second sample into said second sample container from said first sample container, said information regarding the sample contained in said first sample container being stored in said first information recording medium provided on said first sample container; and
   a second information reader/writer, attached to the transportation mechanism, for copying at least a part of information regarding the second sample contained in said second sample container into one of said second information recording medium provided on a container holding tank from another said second information recording medium provided on another container holding tank at the time of a transfer operation of said transfer mechanism to transfer said second sample container to another of said container holding tanks.

2. An automatic analyzer according to claim 1, wherein said second information recording medium is a radio tag.

3. Analysis apparatus according to claim 1, wherein said container holding tanks include at least one of a pipetting-step container holding tank, a mixing-step container holding tank, and an analysis-step container holding tank.

4. Analysis apparatus according to claim 1, wherein each of said container holding tanks is configured to perform one function of a temperature management function and a stirring function.

* * * * *